United States Patent [19]
Stark et al.

[11] Patent Number: 6,041,889
[45] Date of Patent: Mar. 28, 2000

[54] STETHOSCOPE HEAD COVER DISPENSING ARRANGEMENT

[76] Inventors: Wayne T. Stark, 4787 Yorkshire Way, Granite Bay, Calif. 95746; Raymond J. Mikelionios, 203 Grove St., Roseville, Calif. 95678

[21] Appl. No.: 08/948,018

[22] Filed: Oct. 10, 1997

[51] Int. Cl.[7] ........................................................ A61B 7/02
[52] U.S. Cl. ............................................ 181/131; 181/137
[58] Field of Search ...................................... 181/131, 137; 600/528; 381/67

[56] References Cited

U.S. PATENT DOCUMENTS

| | | | |
|---|---|---|---|
| 5,448,025 | 9/1995 | Stark et al. | 181/131 |
| 5,528,004 | 6/1996 | Wurzburger | 181/131 |

*Primary Examiner*—Khanh Dang
*Attorney, Agent, or Firm*—Don Finkelstein

[57] ABSTRACT

A plurality of single diaphragm cover dispensable assemblies (11) each of which has a stethoscope diaphragm cover (12) having a thin plastic body member (16) to which there is applied a pressure sensitive adhesive layer (26) mounted on an adhesive protective layer (14) on a first surface (30). A stacking pressure sensitive adhesive layer (34) is on the adhesive protective layer (14) in a location spaced from the portion (28B) attached to the cover (12). The stacking pressure sensitive adhesive layer 34 may be on the first surface (30) or the second surface (32) of the adhesive protective layer (14). A plurality of the assemblies (11) are in a stacked aligned array with the stacking pressure sensitive adhesive layers (34) providing the detachable coupling of one assembly (11) to the next assembly (11) in the stack.

18 Claims, 4 Drawing Sheets

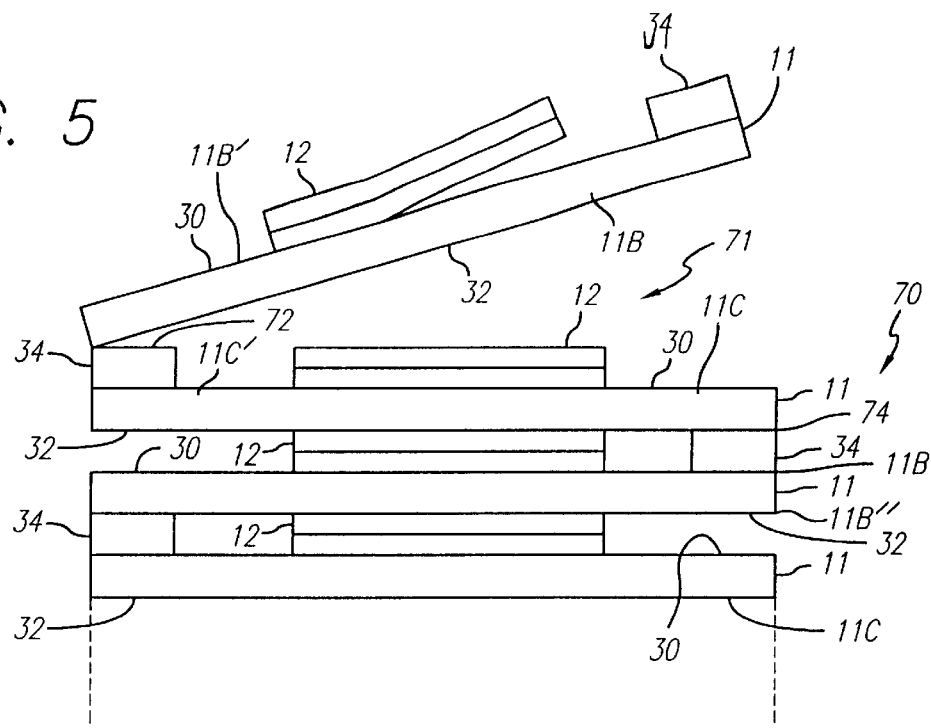

STETHOSCOPE HEAD COVER DISPENSING ARRANGEMENT

BACKGROUND OF THE INVENTION

1. Field of the Invention

This invention relates to the dispensing art and more particularly to an improved arrangement for supplying a plurality of covers for a stethoscope head diaphragm and which allows the convenient selective removal of a single cover as required.

2. Background of the Invention

A number of structural arrangements have been proposed and/or utilized as disposable covers for the head of a stethoscope. These covers are utilized to prevent the contamination of the diaphragm of the stethoscope head from the ambient environment as well as patient to patient contamination from the head of the stethoscope. One such cover for a stethoscope head is shown in our U.S. Pat. No. 5,448,025. Such a cover for a stethoscope head as disclosed therein, and as disclosed in other patents including some of the prior art patents mentioned therein is generally comprised of a body member having a thin sheet of plastic, usually circular in shape to conform to the shape of the diaphragm of the stethoscope. The body member also comprises a layer of a peelable, pressure sensitive adhesive applied to one surface of the plastic sheet. An adhesive protective layer is generally applied to the pressure sensitive adhesive layer to protect the adhesive during shipping, storage and handling of the cover before the use thereof. The adhesive protective layer is removed from the adhesive and discarded when it is desired to mount the cover on the head of the stethoscope. The cover is then applied by pressing the pressure sensitive adhesive to the diaphragm of the stethoscope and the thin plastic sheet is pressed against the desired portion of the anatomy of the patient during use of the stethoscope. After the examination of the patient is concluded, the cover is discarded.

Since there are a very large number of separate utilizations by, for example, a medical practitioner, of a stethoscope on different patients during the course of a day, for safety a large number of stethoscope head covers must be available to the medical practitioner. In those applications where the medical practitioner is at a permanent location, a dispensing arrangement consisting of a large roll of covers mounted on a suitable adhesive protective layer, as disclosed in our U.S. Pat. No. 5,448,025 is quite satisfactory for convenient use by the medical practitioner. However, in many applications such as when the medical practitioner is performing the rounds of a large number of patients in a hospital, where the medical practitioner makes a house call or even where the medical practitioner has several examination rooms in the medical office, carrying a large role, or even a smaller sized role of such diaphragm head covers is impractical.

Thus, there has long been a need for a stack of a large number of stethoscope diaphragm head covers which may be conveniently carried and which allows rapid and easy removal of a single cover from the stack as required when the stethoscope is to be utilized.

SUMMARY OF THE INVENTION

Accordingly, it is an object of the present invention to provide a stacked aligned array of a plurality of stethoscope diaphragm head covers.

It is another object of the present invention to provide such a stacked, aligned array of a plurality of stethoscope diaphragm head covers which may be conveniently carried.

It is yet another object of the present invention to provide such a stacked, aligned array of stethoscope diaphragm head covers in a "book" type aligned array and in a "fan" type aligned array.

The above and other object of the invention are achieved, according to preferred embodiments thereof, by providing a plurality of single stethoscope diaphragm cover dispensable assemblies. Each of the assemblies has a stethoscope diaphragm cover that is mounted on a removable adhesive protective layer. The stethoscope cover is generally comprised of a thin, flexible membrane-like body member of a plastic having a thickness of on the order of 0.1 mm (millimeter) to 0.4 mm. The flexible stethoscope diaphragm cover may be of the type, for example, disclosed in our U.S. Pat. No. 5,448,025, though the principles of the present invention may be utilized in dispensing arrangements for other devices which may be similar to the cover 12.

The stethoscope cover also has a peelable, pressure sensitive adhesive layer on the body member. The pressure sensitive adhesive layer is detachably mountable onto a stethoscope head for detachably adhering to, at least, the diaphragm of a stethoscope head. The use and construction of a diaphragm cover which may be utilized in the present invention is shown, for example, in our U.S. Pat. No. 5,448,025. Thus, the cover described herein is utilized herein as an illustrative type of structure which may be conveniently dispensed according to the principles of the present invention and is not limiting on the general application of the present invention.

The removable adhesive protective layer is detachably mounted on the pressure sensitive adhesive layer of the cover in a manner well known in the pressure sensitive adhesive art. The adhesive protective layer has a margin portion extending outwardly from the portion of the adhesive protective layer which is adhered to the cover. The adhesive protective layer has a first surface and a second surface and the cover, in a preferred embodiment of the present invention, is detachably mounted on the first surface of the adhesive protective layer.

A stacking pressure sensitive adhesive layer is applied to the first surface of the adhesive protective layer on the first surface in a location thereon spaced from the portion thereof attached to the cover. The stacking pressure sensitive adhesive layer provides the detachable coupling for the stacked alignment array of a plurality of the single stethoscope diaphragm cover dispensable assemblies.

A plurality of such assemblies are coupled together in a stacked aligned array by the stacking pressure sensitive adhesive layer. To provide a "book" type aligned array, the assemblies are place with the corresponding stacking pressure sensitive adhesive layers in the same location throughout the stack. To provide a "fan" type stacked aligned array, alternate assemblies are rotated 180°. In other embodiments of the present invention, the cover is on the first surface of the removable adhesive protective layer and the stacking pressure sensitive adhesive layer is on the second surface of the removable adhesive protective layer. A plurality of such assemblies may be coupled together in either a "book" type or a "fan" type stacked array as above described.

Another embodiment of the present invention incorporates a plurality of double stethoscope diaphragm cover dispensable assemblies in which a diaphragm cover is on each side of a single adhesive protective layer. Such an arrangement is particularly useful in those applications wherein two stethoscopes may be used and the heads of the stethoscopes may be of different sizes. In such applications, each of the diaphragm covers may be contoured to accommodate the size of each of the stethoscope heads. Similarly, more than one diaphragm cover may be placed on the same side of the adhesive protective layer and such diaphragm covers may be of the same contours or different contours as may be desired for particular applications.

BRIEF DESCRIPTION OF THE DRAWING

The above and other objects of the present invention may be more fully understood from the following detailed description taken together with the accompanying drawing wherein similar reference characters refer to similar elements throughout. The various Figures of the Drawing are not necessarily to scale in order that the features and advantages of the present invention may be more clearly understood.

FIG. 5 illustrates a dispensing arrangement according to the principles of the present invention comprised of a fan type stacked array of a plurality of the stethoscope diaphragm cover dispensable assemblies as depicted in FIG. 1;

FIG. 6 illustrates a dispensing arrangement according to the principles of the present invention comprised of a fan type stacked array of a plurality of the stethoscope diaphragm cover dispensable assemblies as depicted in FIG. 2;

DESCRIPTION OF THE PREFERRED EMBODIMENTS

Figure 1:
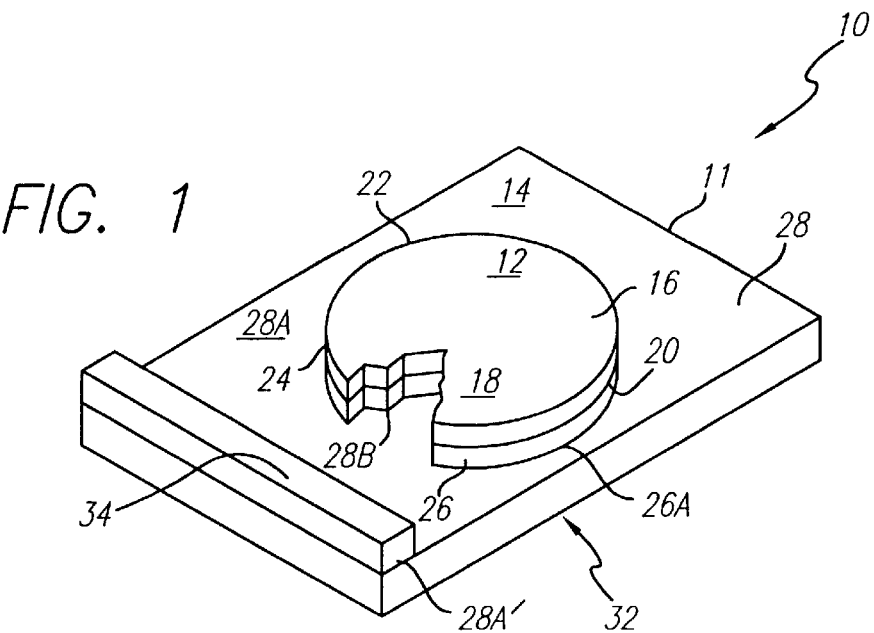
FIG. 1 is a perspective view of an embodiment of the present invention showing a single stethoscope diaphragm cover dispensable assembly comprised of a stethoscope diaphragm cover as mounted on a removable adhesive protective layer.

As utilized herein, the terms "top", "bottom", "side", "front", "back", "first" and/or "second" are used for clarity in description and are not limiting on the general construction of the invention according to the principles thereof. Further, while the covers of the present invention are referred to as "diaphragm covers" for the head of the stethoscope, such covers also, in preferred embodiments, cover, in addition to the diaphragm, the rim portion of the stethoscope which surrounds the diaphragm and/or other portions of the diaphragm head which may come into contact with the person under examination.

As noted above, the depiction of the preferred embodiments of the present invention as shown on the drawing are not necessarily to scale in order that the features of the present invention as well as the functional inter-relationship between the various elements of the structure of the present invention may be more easily understood. In particular, the relative thicknesses of the various components of the embodiments illustrated in the drawing are not to scale and the thicknesses of certain of the elements has been enlarged to show clearly the functional relationships.

Referring now to the drawing, there is illustrated in FIG. 1 an embodiment 10 of the present invention showing a single stethoscope diaphragm cover dispensable assembly 11 having a stethoscope diaphragm cover 12 that is mounted on a removable adhesive protective layer 14. The stethoscope cover 12 is generally comprised of a thin, flexible membrane-like body member 16 of a plastic having a thickness of on the order of 0.1 mm (millimeter) to 0.4 mm and having an upper surface 18, a lower surface 20 and a cover peripheral edge 22 having a first predetermined geometrical configuration as indicated at 24. The flexible stethoscope diaphragm cover 12 may be of the type, for example, disclosed in our U.S. Pat. No. 5,448,025, though the principles of the present invention may be utilized in dispensing arrangements for other devices which may be similar to the cover 12.

The first predetermined geometrical configuration 24 is selected to match the contour of a stethoscope head to which it is to be applied. Such contour is generally round, but oval or other shapes may be included in the stethoscope heads available. Thus, the first preselected geometrical configuration may be any configuration desired to match a particular stethoscope head contour.

The stethoscope cover 12 also has a peelable, pressure sensitive adhesive layer 26 on the lower surface 20 of body member 16 and the pressure sensitive adhesive layer 26 has a lower surface 26A for detachably mounting onto a stethoscope head for detachably adhering to, at least, the diaphragm of a stethoscope head. The use and construction of a diaphragm cover which may be utilized in the present invention is shown, for example, in our U.S. Pat. No. 5,448,025. The present invention is not limited to utilization of the particular configuration of a stethoscope diaphragm cover as shown in our U.S. Pat. No. 5,448,025 for the improved dispensing arrangement herein but other designs of stethoscope diaphragm covers or similar structures whether for stethoscope diaphragm covers or for other utilizations may be advantageously employed in the present invention. Thus, the cover 12 is utilized herein as an illustrative type of structure which may be conveniently dispensed according to the principles of the present invention and is not limiting on the general application of the present invention.

A central portion 28B of the removable adhesive protective layer 14 is detachably mounted on the lower surface 26A of the peelable, pressure sensitive adhesive layer 26. The adhesive protective layer 14 also has a margin portion 28A extending outwardly from the central portion 28B of the adhesive protective layer 28. The adhesive protective layer 14 has a first surface 30 and a second surface 32 and a peripheral edge 34 defining a second predetermined geometrical configuration. The cover 12 in the embodiment 10 is detachably mounted on the first surface 30 of adhesive protective layer 14. In the embodiment 10 the second predetermined geometrical configuration is a rectangular quadrilateral. However, the second predetermined geometrical configuration of the peripheral edge may be any desired configuration such as square, hexagonal, round or the like. and may, if desired, be the same geometrical configuration as the first predetermined geometrical configuration of the cover 12.

A stacking pressure sensitive adhesive layer 34 is applied to the first surface 30 of adhesive protective layer 14 on a part 28A' of the margin portion 28A. The stacking adhesive layer 34 provides the detachable coupling for the stacked alignment array of a plurality of the single stethoscope diaphragm cover dispensable assemblies 11, as described below in greater detail. The stacking pressure sensitive adhesive layer 34 may be placed on other portions of the first surface 30 of margin portion 28A as may be desired in particular applications.

Figure 2:
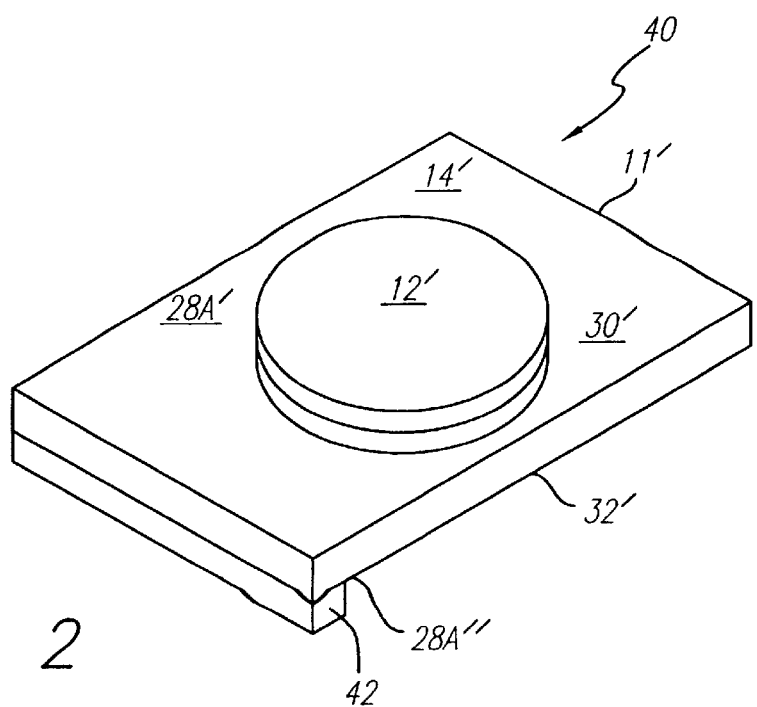
FIG. 2 is a perspective view of another embodiment of the present invention showing a single stethoscope diaphragm cover dispensable assembly of a stethoscope diaphragm cover mounted on a removable adhesive protective cover which differs from the adhesive protective cover shown in FIG. 1.

FIG. 2 illustrates an embodiment 40 of a single stethoscope diaphragm cover dispensable assembly 11' of the present invention which is generally similar to the single stethoscope diaphragm cover dispensable assembly 11 of embodiment 10 and has a stethoscope cover 12' detachably mounted on a first surface 30' in the margin portion 28A' of a removable adhesive protective layer 14'. The removable adhesive protective layer 14' has a second surface 32'. In the embodiment 40 a stacking pressure sensitive adhesive layer 42, which may be similar to stacking pressure sensitive adhesive layer 34 described above is applied on the second surface 32' of the removable adhesive protective layer 14' as indicated at 28A". Thus, in the embodiment 40, the cover 12' is on the first surface 30' of adhesive protective layer 14 and the stacking pressure sensitive adhesive layer 42 is on the second surface 32' of adhesive protective layer 14' while in the embodiment 10 both the stacking pressure sensitive adhesive layer 34 and the cover 12 are on the first surface of the adhesive protective layer 14. Both the single stethoscope diaphragm cover dispensable assembly 11 and 11' may advantageously utilized in an aligned stacking arrangement according to the principles of the present invention.

Figure 3:
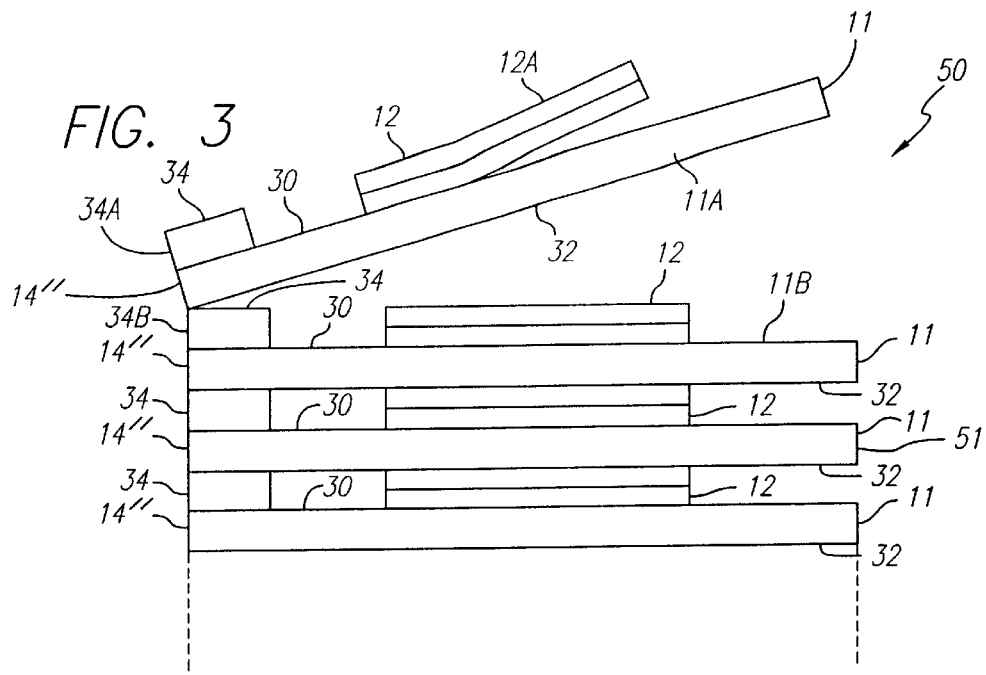
FIG. 3 illustrates a dispensing arrangement according to the principles of the present invention comprised of a book type stacked array of a plurality of the stethoscope diaphragm cover dispensable assemblies as depicted in FIG. 1; and, FIG. 4 illustrates a dispensing arrangement according to the principles of the present invention comprised of a book type stacked array of a plurality of the stethoscope diaphragm cover dispensable assemblies as depicted in FIG. 2.

FIG. 3 illustrates an embodiment, generally designated 50 of a plurality of stacked, single stethoscope diaphragm cover dispensable assemblies 11 as shown in FIG. 1 in a predetermined stacked alignment array 51. While four of such assemblies 11 are shown on FIG. 3, several hundred may be included in the stacked array 51 of embodiment 50. The stacked array 51 is a "book" type array in that all of the assemblies 11 are detachably couple together at the edges 14" of adhesive protective layer 14.

Each of the stacking adhesive layers 34 are mounted on the first surface 30 of adhesive protective layer 14 and are detachably adhered to the second surface 32 of the next assembly 11. The assembly 11A is shown in the position where it has been almost detached from the stacking adhesive layer 34B of assembly 11B and the cover 12 is partially removed from the first surface 30 of adhesive protective layer 14. As shown in FIG. 3, all of the assemblies 11 have the stacking pressure sensitive adhesive layer 34 in the corresponding location on the adhesive protective layer 14. In the embodiment 50, each of the assemblies may be removed from the stacked array 51 as required and the entire stacked array 51 may be conveniently carried in the pocket or purse of the medical practitioner, in the medical bag of the medical practitioner or in some similar carrying case. The stacked array 11 may be on the order of 2 inches to 4 inches square and may be on the order of ½ inch to 1 inch thick depending upon the number of assemblies 11 in the array.

Figure 4:
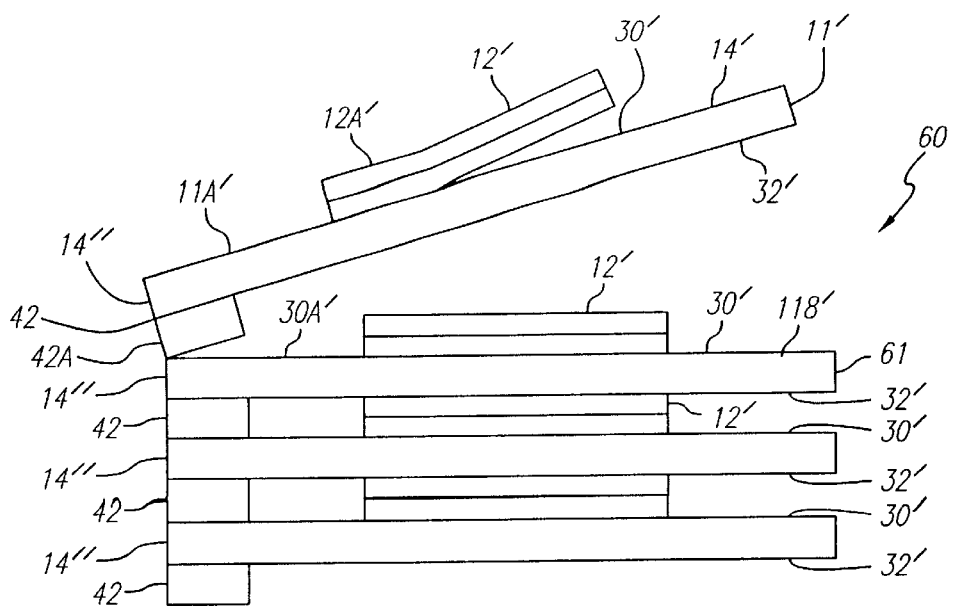

FIG. 4 illustrates an embodiment, generally designated 60 of a plurality of stacked, single stethoscope diaphragm cover dispensable assemblies 11' as shown in FIG. 2 in a predetermined stacked alignment array 61. The embodiment 60 of FIG. 4 may be generally similar to the embodiment 50 but is comprised of a plurality of the assemblies 11' of FIG. 2 rather than a plurality of the assemblies 11 of FIG. 1. While four of such assemblies 11' are shown on FIG. 4, several hundred may be included in the stacked array 61 of embodiment 60. The stacked array 61 is also a "book" type array in that all of the assemblies 11' are detachably couple together at the edges 14" of adhesive protective layer 14'.

Each of the stacking adhesive layers 42 are mounted on the second surface 32 of adhesive protective layer 14' and are detachably adhered to the first surface 30 of the next assembly 11'. The assembly 11A' is shown in the position where stacking adhesive layer 42A has been almost detached from the first surface 30A' of assembly 11B' to allow removal of assembly 11A' from the stack 61 and the cover 12A' is partially removed from the first surface 30' of adhesive protective layer 14'. As shown on FIG. 4, all of the assemblies 11' have the stacking pressure sensitive adhesive layer 42 in the corresponding location on the adhesive protective layer 14'. In the embodiment 60, each of the assemblies 11' may be removed from the stacked array 61 as required and the entire stacked array 61 may be conveniently carried in the pocket or purse of the medical practitioner, in the medical bag of the medical practitioner or in some similar carrying case. The stacked array 11' may be on the order of 2 inches to 4 inches square and may be on the order of ½ inch to 1 inch thick depending upon the number of assemblies 11' in the array.

Both the embodiments 50 of FIG. 3 and the embodiment 60 of FIG. 4 are an aligned stacked array of the "book" type in that each of the assemblies is connected at the same edge of the adhesive protective layer. In some applications of the present invention, however, it has been found advantageous to utilize a "fan" or accordion stacked array. Both the assembly 11 of FIG. 1 and the assembly 11' of FIG. 2 may be formed into an aligned "fan" type stacked array.

FIG. 5 illustrates an embodiment 70 of a plurality of the assemblies 11 of FIG. 1 in a stacked, fan type alignment array generally indicated at 71. The embodiment 70 is generally similar to the embodiment 50 described above. The stacking pressure sensitive adhesive layers 34 are on the first surfaces 30 of the removable adhesive protective layers 14 and the diaphragm covers 12 are on the first surfaces 30 of the adhesive protective layers 14. In embodiment 70, the assemblies 11 are in two groups. In the first group there are assemblies 11B and in the second group there are the assemblies 11C which are alternately positioned between the assemblies 11B in the stacked array 71. Assembly 11B' is shown partially removed from the stacked array 71 as it is peeled from the stacking pressure sensitive adhesive layer 34 of the adjacent assembly 11C' as indicated at 72. Similarly, assembly 11C' will separate from the stacking adhesive layer 34 of the assembly 11B" at 74. Each of the assemblies 11B are the same as the assemblies 11C except they are rotated 180° from the orientation of the assemblies 11B.

FIG. 6 illustrates an embodiment 80 of a plurality of the assemblies 11' of FIG. 2 in a stacked, fan type alignment array generally indicated at 81. The embodiment 80 is generally similar to the embodiment 70 described above. The stacking pressure sensitive adhesive layers 42 are on the second surfaces 32' of the removable adhesive protective layers 14' and the diaphragm covers 12' are on the first surfaces 30' of the adhesive protective layers 14'. In embodiment 80, the assemblies 11' are in two groups. In the first group there are assemblies 11'B and in the second group there are the assemblies 11'C which are alternately positioned between the assemblies 11'B in the stacked array 81. Assembly 11'B' is shown partially removed from the stacked array 71 as it is peeled from the stacking pressure sensitive adhesive layer 34 of the adjacent assembly 11'C' as indicated at 72'. Similarly, assembly 11'C' will separate from the stacking adhesive layer 34 of the assembly 11'B" at 74'. Each of the assemblies 11'B are the same as the assemblies 11'C except they are rotated 180° from the orientation of the assemblies 11'B.

The embodiments 70 and 80 may have the same number of assemblies in the stacked alignment array and have the same dimensions as the embodiments 50 and 60 as above described.

Figure 7:
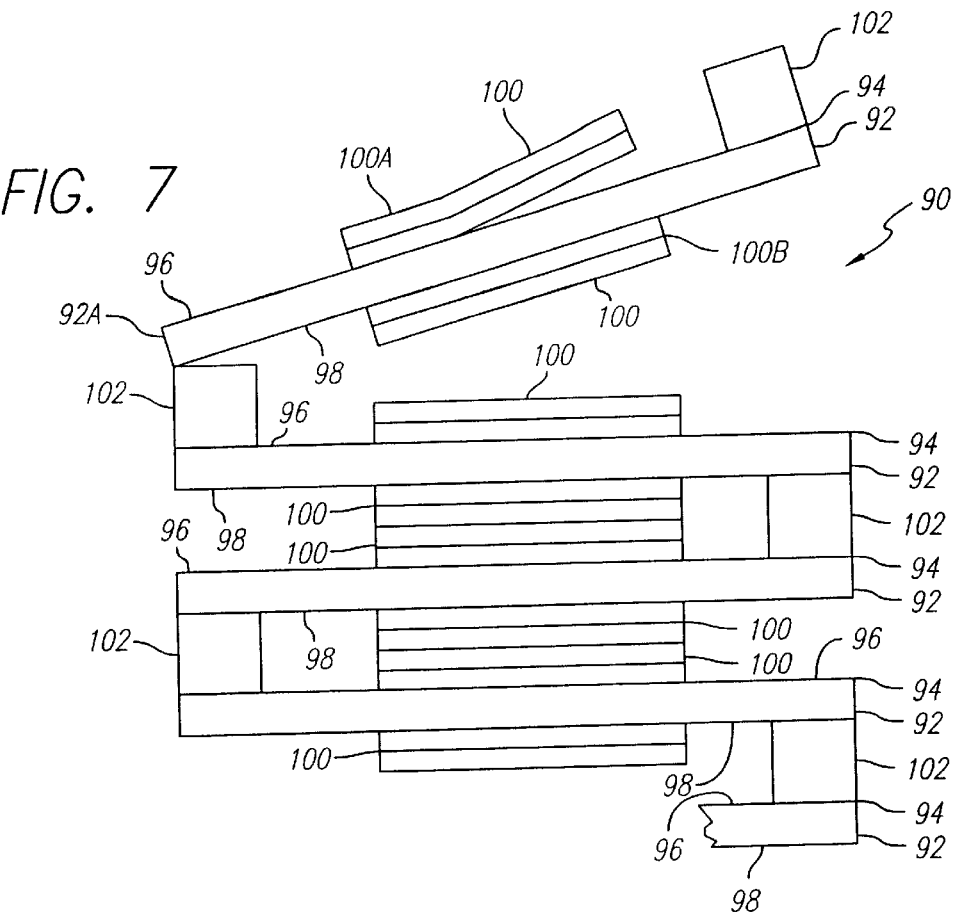
FIG. 7 illustrates another embodiment of the present invention.

In some applications it may be desirable to have a plurality of diaphragm covers on each of the adhesive protective layers. For example, in those applications wherein several different stethoscopes may be utilized which have different sized or configured heads and/or diaphragms, several of the appropriate diaphragm covers may be included on one adhesive protective layer with each diaphragm cover contoured to fit on a particular stethoscope head. FIG. 7 illustrated an embodiment 90 of the present invention in which there is provided a plurality of stacked assemblies 92 each of which assemblies 92 is comprised of an adhesive protective layer 94 having a first surface 96 and a second surface 98. A disposable stethoscope diaphragm cover 100 is provide on each of the first and second sides of the adhesive protective layers 92 and the diaphragm covers 100 may be the same as the diaphragm covers 12 and 12' described above and may be of the same shape and contour or may be of different shapes and contours on each side of the. That is, each of the assemblies 92 may have two of the same size and contour diaphragm covers or may have two diaphragm covers which are of different shapes and contours. For example, on assembly 92A the cover 100A may be of one size and/or contour and the cover 100B may be of the same or a different size and/or contour.

Each of the assemblies 92 is also provided with a stacking pressure sensitive adhesive layer 102 on one of the first or second surfaces 96 and 98 of the adhesive protective layer. As shown on FIG. 7, the stacking pressure sensitive adhesive layers 102 are on the first surface 96 of the adhesive protective layers. the assemblies 92 may be connected together in either the fan type dispensing arrangement as shown on FIG. 7 or in a book type dispensing arrangement similar to that illustrated above in FIGS. 3 and 4.

Figure 8:
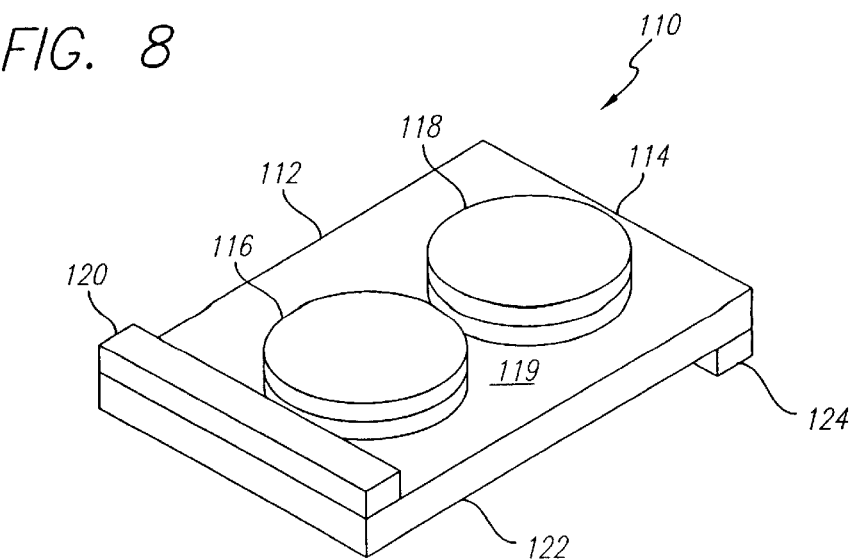
FIG. 8 illustrates another embodiment of the present invention.

FIG. 8 illustrates an embodiment 110 of an assembly 112 useful in the practice of the present invention. In the embodiment 110, the assembly 112 has an adhesive protective layer 114 similar to the adhesive protective layers 11, 11' and 92 described above and there is provided two diaphragm covers 116 and 118 on the first surface 119 of the adhesive protective layer 114. The diaphragm covers 116 and 118 may be the same size and configuration or may be of different sizes and configurations as desired for particular applications. A pressure sensitive adhesive layer 120 is also provided on the first surface 119 of the adhesive protective layer 114 and may be the same as the pressure sensitive adhesive layers described above. A plurality of assemblies 112 may be stacked together in either the book type or fan type dispensing arrangements as above described. If desired, one or more diaphragm covers (not shown on FIG. 8) similar to diaphragm covers 116 and 118 may also be provided on the second surface 122 of adhesive protective layer 114 similar to the structure described above in connection with the embodiment 90 described above. A pressure sensitive adhesive layer 124 may, if desired, be provided on the second surface 122 of adhesive protective layer 114.

The various assemblies of diaphragm covers as above described may be combined in the various structural configurations of stacked dispensing arrangements as described above and as illustrated on the drawing as may be desired for particular applications.

This concludes the description of the present invention. From the above it can be seen that there is provided a convenient stacked array comprised of a plurality of assemblies of stethoscope diaphragm covers which may be conveniently carried by the medical practitioner and the individual assemblies quickly and easily removed from the aligned stack as required when a stethoscope is utilized.

Those skilled in the art may find many variations and adaptations of the present invention and the appended claims are intended to cover all such variations and adaptations falling within the true scope and spirit thereof.

What is claimed is:

1. A dispensing apparatus for selectively dispensing a detachable stethoscope diaphragm cover from a plurality of stacked detachable stethoscope diaphragm covers comprising, in combination:
   a plurality of stacked, stethoscope diaphragm cover dispensable assemblies in a predetermined stacked alignment array, each of said plurality of stacked, stethoscope diaphragm cover dispensable assemblies comprising, in combination:
      at least one detachable stethoscope diaphragm cover comprising:
         a thin, flexible membrane-like body member having an upper surface, a lower surface and a cover peripheral edge, said cover peripheral edge having a first predetermined geometrical configuration substantially matching the geometrical configuration of the stethoscope diaphragm head;
         a peelable, pressure sensitive adhesive layer on said lower surface of said body member for detachably adhering to at least the diaphragm of the stethoscope head for the stethoscope having the condition of the cover installed thereon;
      a plurality of removable adhesive protective layers, each having a first surface, a second surface and a protective layer peripheral edge defining a second predetermined geometrical configuration, and each of said removable adhesive protective layer, having:
         a central portion, and said central portion of said first surface of each of said removable adhesive protective layers detachably adhered to said peelable, pressure sensitive adhesive layer on said at least one of said plurality of detachable stethoscope diaphragm covers;
         a margin portion, and said margin portion of each of said plurality of removable adhesive protective layers extending in regions outside said cover peripheral edge and bounded by said protective layer peripheral edge;
      a stacking pressure sensitive adhesive layer on at least a part of said margin portion of one of said first and second surfaces of each of said plurality of removable adhesive protective layers and on the corresponding part of the margin portion of one of said first surface and second surface on each of said plurality of removable adhesive protective layers;
      and said stacking pressure sensitive adhesive layer on each of said plurality of removable adhesive protective layers detachably adhered to the adjacent removable adhesive protective layer on the other of said first surface and said second surface thereof,
   whereby each of said stethoscope diaphragm covers with a removable adhesive protective layer thereon may be selectively removed from the stacked alignment array.

2. The apparatus defined in claim 1 wherein:

said first predetermined geometrical configuration of said peripheral edge of each of each of said plurality of said body members is different from said second predetermined geometrical configuration of said peripheral edge of each of said plurality of removable adhesive protective layers.

3. The apparatus defined in claim 1 wherein:

said first predetermined geometrical configuration of said peripheral edge of each of each of said plurality of said body members is the same geometrical configuration as said second predetermined geometrical configuration of said peripheral edge of each of said plurality of removable adhesive protective layers.

4. The apparatus defined in claim 2 wherein:

said first predetermined geometrical configuration is circular and said second predetermined geometrical configuration is quadrilateral.

5. The apparatus defined in claim 2 wherein:

said first predetermined geometrical configuration is circular and said second predetermined geometrical configuration is rectangular.

6. The apparatus defined in claim 2 wherein:

said first predetermined geometrical configuration is circular and said second predetermined geometrical configuration is square.

7. The apparatus defined in claim 1 wherein:

said stacking pressure sensitive adhesive layer is on at least a corresponding part of said margin portion of said first surface of each of said plurality of removable adhesive protective layers to provide a book stacking arrangement in said predetermined stacked alignment array.

8. The apparatus defined in claim 1 wherein:

said stacking pressure sensitive adhesive layer is on at least a corresponding part of said margin portion of said second surface of each of said plurality of removable adhesive protective layers to provide a book stacking arrangement in said predetermined stacked alignment array.

9. The apparatus defined in claim 1 wherein:

said stacking pressure sensitive adhesive layer is on a corresponding first part of said margin portion of said second surface of a first group of said plurality of removable adhesive protective layers and on a corresponding second part of said margin portion different from said first part of said margin portion of said second surface on each of a second group of said removable adhesive protective layers and said first group of said plurality of removable adhesive protective layers is alternately positioned between said removable adhesive protective layers of said second group to provide a fan stacking arrangement in said predetermined stacked alignment array.

10. The apparatus defined in claim 7 wherein:

said first predetermined geometrical configuration is circular and said second predetermined geometrical configuration is quadrilateral.

11. The apparatus defined in claim 8 wherein:

said first predetermined geometrical configuration is circular and said second predetermined geometrical configuration is quadrilateral.

12. The apparatus defined in claim 1 wherein:

said stacking pressure sensitive adhesive layer is on a corresponding first part of said margin portion of said first surface of a first group of said plurality of removable adhesive protective layers and on a second part of said margin portion different from said first part of said margin portion of said first surface on each of a second group of said removable adhesive protective layers and said first group of said plurality of removable adhesive protective layers is alternately positioned between said removable adhesive protective layers of said second group to provide a fan stacking arrangement in said predetermined stacked alignment array.

13. The apparatus defined in claim 1 and further comprising:

at least a second stethoscope diaphragm cover is detachably mounted on at least some of said adhesive protective layers.

14. The apparatus defined in claim 13 wherein:

said at least a second stethoscope diaphragm cover is on said first surface of said adhesive protective layer in at least some of said assemblies.

15. The apparatus defined in claim 13 wherein:

said at least a second stethoscope diaphragm cover is on said second surface of said adhesive protective layer in at least some of said assemblies.

16. A stethoscope diaphragm cover dispensable apparatus comprising, in combination:

a stethoscope diaphragm cover comprising:

a thin, flexible membrane-like body member having an upper surface, a lower surface and a cover peripheral edge, said cover peripheral edge having a first predetermined geometrical configuration substantially matching the geometrical configuration of the stethoscope diaphragm head;

a peelable, pressure sensitive adhesive layer on said lower surface of said body member for detachably adhering to at least the diaphragm of the stethoscope head for the condition of the cover installed thereon;

a removable adhesive protective layer, having a first surface, a second surface and a protective layer peripheral edge defining a second predetermined geometrical configuration, and said removable adhesive protective layer, having:

a central portion, and said central portion of said first surface of each of said removable adhesive protective layers detachably adhered to said peelable, pressure sensitive adhesive layer on said stethoscope diaphragm cover;

a margin portion, and said margin portion of said removable adhesive protective layer extending in regions outside said cover peripheral edge and bounded by said protective layer peripheral edge;

a stacking pressure sensitive adhesive layer on at least a part of said margin portion of one of said first and second surfaces of said removable adhesive protective layer.

17. The apparatus defined in claim 16 wherein:

said stacking pressure sensitive adhesive layer is on at least a part of said margin portion of said first surface of said removable adhesive protective layer.

18. The apparatus defined in claim 16 wherein:

said stacking pressure sensitive adhesive layer is on at least a part of said margin portion of said second surface of said removable adhesive protective layer.

* * * * *